United States Patent
Tishin et al.

(10) Patent No.: US 9,017,713 B2
(45) Date of Patent: Apr. 28, 2015

(54) MAGNETIC CARRIER AND MEDICAL PREPARATION FOR CONTROLLABLE DELIVERY AND RELEASE OF ACTIVE SUBSTANCES, METHODS OF THEIR PRODUCTION AND METHODS OF TREATMENT USING THEREOF

(76) Inventors: Aleksandr Mettalinovich Tishin, Troitsk (RU); Juri Alekseevich Rochev, Serpukhovsky raion (RU); Aleksandr Vladimirovich Gorelov, Serpukhovsky raion (RU)

(*) Notice: Subject to any disclaimer, the term of this patent is extended or adjusted under 35 U.S.C. 154(b) by 1000 days.

(21) Appl. No.: 12/421,673

(22) Filed: Apr. 10, 2009

(65) Prior Publication Data
US 2009/0258073 A1 Oct. 15, 2009

(30) Foreign Application Priority Data

Oct. 13, 2006 (RU) ................................ 2006136148
Dec. 29, 2006 (WO) ................ PCT/RU2006/000719

(51) Int. Cl.
*A61F 2/00* (2006.01)
*A61M 37/00* (2006.01)
*A61K 9/00* (2006.01)
*A61K 9/50* (2006.01)
*A61K 41/00* (2006.01)
*B22F 1/00* (2006.01)
*B82Y 30/00* (2011.01)
*C22C 1/04* (2006.01)

(52) U.S. Cl.
CPC .............. *A61M 37/00* (2013.01); *A61K 9/0009* (2013.01); *A61K 9/5094* (2013.01); *A61K 41/0052* (2013.01); *B22F 1/0018* (2013.01); *B22F 1/0059* (2013.01); *B82Y 30/00* (2013.01); *C22C 1/0491* (2013.01); *C22C 2202/02* (2013.01); *B22F 2001/0033* (2013.01); *B22F 2998/00* (2013.01)

(58) Field of Classification Search
CPC .................................. A61K 9/70; A61K 47/02
USPC .......................................................... 424/426
See application file for complete search history.

(56) References Cited

U.S. PATENT DOCUMENTS

| 2005/0074589 | A1* | 4/2005 | Pan et al. ................. 428/206 |
| 2005/0175702 | A1  | 8/2005 | Muller-Schulte |
| 2007/0148437 | A1  | 6/2007 | Muller-Schulte |

FOREIGN PATENT DOCUMENTS

| EP | 1803467 | 7/2007 |
| WO | 9959556 | 11/1999 |
| WO | 03026618 | 4/2003 |
| WO | 2005042142 | 12/2005 |
| WO | 2006022340 | 3/2006 |

* cited by examiner

Primary Examiner — Benjamin Packard

(57) ABSTRACT

The present invention relates to magnetic carriers and medical preparations for controllable delivery and release of active substances. The carrier for active substances comprises material A, which is magnetically or electrically sensible, and material B capable of controlling the retention/release rate of the said active substance from the said carrier, the said retention/release rate being temperature dependent; wherein the material B is in thermal contact with material A, and wherein the material A has magnetocaloric or electrocaloric effect sufficient to substantially vary the said retention/release rate of the active substance from the carrier. The invention further provides methods for controllable delivery and release of active substances in a predetermined place and at a predetermined time, and methods of treatment using these carriers. Methods of production of magnetic carriers are also proposed.

9 Claims, No Drawings

MAGNETIC CARRIER AND MEDICAL PREPARATION FOR CONTROLLABLE DELIVERY AND RELEASE OF ACTIVE SUBSTANCES, METHODS OF THEIR PRODUCTION AND METHODS OF TREATMENT USING THEREOF

CROSS-REFERENCE TO RELATED APPLICATIONS

This application claims the benefits from International Application PCT/RU2006/000719 filed on Dec. 29, 2006 and priority application RU 2006136148 filed on Oct. 13, 2006. The contents of these applications are hereby incorporated by reference and in their entirety.

FIELD OF THE INVENTION

The invention relates to medicine, pharmacology and biotechnology, more particular, the invention relates to methods of delivery of medical or therapeutic agents or other bioactive materials to a human organism with its controlled release into an organism.

BACKGROUND OF THE INVENTION

Delivery of pharmaceuticals to target organs in a human organism is one of the basic problems in medicine, pharmaceutics and biotechnology, i.e. in the areas related to treatment of various diseases.

Furthermore, it is often important and even necessary in diagnostics and treatment of diseases to carry out controlled release of one or several compounds into an organism of a patient, in particular, organism of a mammal, for a long period.

However, traditional methods of administration of pharmaceuticals, such as oral intake or direct injection of a pharmaceutical, do not provide long time controlled release of the drug. Instead of providing a controlled concentration of a pharmaceutical during a long period of time, these methods of administration result in the instant release of a drug into an organism and subsequent relatively fast decrease of the concentration in blood. However, in many cases, instant release of a pharmaceutical with subsequent decrease of its level in blood is often not a preferred way of administration. The effectiveness of treatment can be much higher, when the concentration of a pharmaceutical in blood is maintained at a predetermined fixed level during a long period of time or when a pharmaceutical is released at a predetermined moment. Furthermore, instant administration of a pharmaceutical into an organism may cause the increase of its concentration, which exceeds the abilities of active sites to digest it, and may exceed capacity of the metabolic and excretory mechanism of a living organism. If the level of pharmaceutical remains increased, it may affect tissues or organs.

On the contrary, continuous controlled release of a pharmaceutical for a long period of time has essential clinical advantages. For example, when treatment with a pharmaceutical should proceed for a long period of time, administration of a pharmaceutical by intake or direct injection is connected with inconveniences of necessity of recurrent administration. Moreover, when treatment requires recurrent pharmaceutical administration, there is a possibility that a patient forgets or purposely does not take a pharmaceutical. If an opportunity of continuous administration of a pharmaceutical will be provided, so its controlled release during a long period of time will be carried out, necessity of recurrent administration will be eliminated.

Traditional methods of administration of medical materials deeply in biotissues are syringe or needleless injectors, which represent containers with pharmaceutical fluid, wherefrom medical fluid through a syringe needle (or through a throttle hole of injector) under high pressure flows deep in biotissues through broken skin.

However, this classical method of administration of pharmaceuticals does not provide its purposeful delivery to target organs, and neither its controlled release into an organism.

A method of administration (delivery) of a pharmaceutical by applying a medicated pad on a nidus with simultaneous stem of blood flow in the nidus area, and ultrasonic sound exposure for 30 minutes, with a periodic loosing of a tourniquet was disclosed in SU 556805, May 5, 1977.

From SU 882528, Jan. 4, 1979, other method of administration of pharmaceuticals in an organism by a device containing carrying case, container with a medical fluid and an ultrasonic converter, is known. The delivery of pharmaceutical is performed by contact action of high frequency ultrasound on a biotissue in area of pathological nidus through a wad with a pharmaceutical.

Disadvantages of the mentioned methods are that the high-frequency ultrasound, having small amplitudes of radiator head, performs only micromassage of biotissue surface, which does not provide sufficient infiltration of a medical material through an integument, and depth of penetration does not exceed the thickness of skin epidermis.

The method of delivery (administration) of pharmaceuticals to a wounded surface, which comprises spraying of a medical solution in the form of a medical aerosol torch, treated with ultrasound (SU 1106485, Oct. 22, 1982), is known. This method provides penetration of pharmaceuticals only in biotissue areas with a broken horny layer of skin epidermis. Delivery of pharmaceuticals deep into biotissues through intact integument is inconvenient since the horny layer of epidermis serves as a protective barrier, virtually non-permeable for liquids coming from external media.

From RU 2076746, Apr. 10, 1997 the method of administration of pharmaceuticals is known, which comprises spraying of a biotissue with a medical solution in the form of a medical aerosol torch, treated with ultrasound vibration frequency of 44-66 kHz and radiator head vibration amplitude of 25-35 microns and treatment of a biotissue by low-frequency ultrasound with frequency of 26.5 kHz and vibration amplitude of 40-50 microns at exposure 5-10 s sm$^{-2}$. According to the method, a local heating zone is made preliminary above the biotissue surface with temperature 40-50° C., which induces diaphoresis from it. Then the biotissue is promptly cooled with a torch of an aerosol of medical material down to 20-25° C., and treatment with low-frequency ultrasound is performed after spraying a pharmaceutical, and simultaneously with ultrasonic an alternating magnetic field is applied with magnetic induction amplitude of 30-40 mT.

The said methods are designed only for delivery of a medical (therapeutic) agent to external, generally wounded surface of a biotissue, i.e. have limited applications.

From RU 2250102 C2, Apr. 20, 2005 the method of drug administration is known, with directed transfer and subsequent release of a bioactive compound into organism of animals after contact to mucous membranes, especially as method of oral and intrapulmonary administrations. Bioactive compound is encapsulated into a microcapsule made of biocompatible polymer or a copolymer which can pass through a gastrointestinal tract and be conserved on a mucosal surface without destruction, or being exposed to it insignificantly. This provides intake of a bioactive compound into Peyer's patches or others lymphatic tissues associated with mucous membrane and penetration into them in initial effective quantities. The term "biocompatible polymeric material" is designated for a polymer which is not possessing toxicity, carcinogenic or inflammatory action in an organism. It is desirable, that an indifferent polymeric material of microcapsules was exposed to biodegradation, i.e. was decomposed during physiological processes to products which are not accumulated in tissues and excreted from an organism. Microcapsules should have such dimensions and physical and chemical properties, which would provide their effective selective intake into Peyer's patches. In the invention the problems of the directed transfer of bioactive compounds to Peyer's patches and other tissues, associated with mucous membranes and inclusions, are solved.

However, the known method concerns only the method of oral administration of an antigen to animals at which it reaches Peyer's patches and is intaken into them, stimulating, thus, immune system of mucous membrane, without loss of immunifacient activity during transport along a gastrointestinal tract.

The known method of oral administration of a bioactive compound to animals provides its transport and intake into Peyer's patches, for establishment of local or systemic concentration of a drug, but concerns the delivery of a certain pharmacological form of a therapeutic agent, containing a bioactive ingredient and polymeric or copolymeric inert material, preferably exposed to biodegradation, which is applicable for transport to mucous membranes by means of this method.

Various implants have been developed for achievement of a required level of a pharmaceutical in blood during a long period of time, which provide continuous controlled release when administered to a patient.

Implants contain active material or a pharmaceutical in combination with a polymeric system of delivery, which controls release of the pharmaceutical. The pharmaceutical is physically encapsulated in a polymeric matrix and released from a matrix by diffusion through polymer or at break of a polymeric matrix. Generally, polymeric system of delivery is a biocompatible resolving polymeric matrix. The polymeric matrix, however, is not always resolving. When not resolving implants are used, surgical removal of the implant is required after release of a pharmaceutical.

A variety of matrices have been developed for controlled release of a pharmaceutical, including polymeric matrices made of hydrogels, gelatin, cellulose, organopolysiloxane rubbers, polyurethanes, wax, poly(vinyl alcohol), polyglycolic acid and lactic acid polymer. Often polymeric matrix represents a copolymer of lactic acid and a glycolic acid ("PLGA", polymer of lactic glycolic acid). Pharmaceutical is released from the PLGA matrix at matrix hydrolytic cleavage. When polymeric matrix decomposes, the pharmaceutical is released into adjacent fluids of an organism.

Rate of release of a pharmaceutical depends on the set of variables, including, for example, choice of polymeric matrix, concentration of pharmaceutical in the matrix, size and form of an implant, method of implant manufacturing, surface area of implant and pore size.

From RU 2272617, Mar. 27, 2006 the method of controlled release of a pharmaceutical into an organism of a patient is known, comprising administration of a pharmaceutical implant, which includes microparticles of one or several pharmaceuticals dispersed in a resolving polymer, which microparticles are sufficiently interrelated with each other to support the preset implant form without complete sintering of polymer, and in which implant breaks up to separate microparticles at certain time after administration. Such implant is administered intramuscularly or subcutaneously.

Nowadays various physical methods of medical treatment are widely spread in medicine, for example, the methods of magnetotherapy, which are based on action of electromagnetic field and use of various magnetic materials.

For example, from U.S. Pat. No. 5,236,410, 1993 a method of tumors treatment is known, based on the use of magnetic particles together with a therapeutic agent and influence of electromagnetic field. The method comprises selective catheterization of hepatic artery or renal artery at kidney tumor. The dispersion of barium hexaferrite or strontium in oil solution of Dioxadet is injected through a catheter to a tumor area by an external magnetic field under control of a roentgenoscopy. At large tumor sizes an arterial blood stream afterwards is reduced with a metal spiral. In 1-3 days the tumor is attacked with a microwave electromagnetic field or ultrasound for achievement of temperature in the tumor 43-43.50° C. and the treatment continues during 5-45 minutes at this temperature. Puncture biopsy of the tumor is performed in 6-7 and in 15-20 days and, again, in 3-6 months, in presence of viable tumor cells the hyperthermia is repeated.

Such method due to simultaneous impact on tumor cells of a chemical drug and hyperthermia restricts a possibility of release of tumor cells and cellular debris in general blood stream, thus, reducing probability of metastases and intoxication of an organism. Radio-opacity of embolisate allows to control the tumor state and, if necessary, to carry out repeated courses of hyperthermia.

Accordingly, and also in view of other not less important factors, magnetoactive compounds including pharmaceuticals have wide applications.

Delivery of pharmaceuticals to target organs in a human organism is one of the fundamental problems of, for example, chemotherapy. One of the approaches to this problem, as follows from the aforesaid, is the use magnetosensitive carriers for pharmaceuticals, which administrated into blood vessels, transported by blood flow and are localized in a preset place by means of magnetic field. Magnetosensitive and biocompatible nanospheres are known, designed for injection into vessels and localization in a certain place, which consist of a carbohydrate crystalline matrix and magnetic particles (application WO 83/01738, 1983). Carbohydrate crystalline matrix is starch, glycogen, dextran or their derivatives. The known carrier possesses insufficient hydrolytic and enzymatic stability.

Magnetic composite microspheres are also known, based on a net organosilicon polymer, which consist of a core representing magnetizable material with sizes less than $300 \times 10^{-4}$ micron, evenly distributed in a net of polysilsesquioxane, containing more than 2 vinyl groups in a molecule and probably ionogenic and/or non-vinyl active group and a surface layer, representing net silicon organic polymer—application EPO 0435785, 1991. However the polymeric matrix of the known carrier possesses insufficient biocompatibility.

Other method of intravenous administration of biologically destructed magnetosensitive carrier, containing magnetic particles, covered with a polymeric matrix (U.S. Pat. No. 4,247,406, 1981) is known. The carrier contains $Fe_3O_4$ as magnetic particles and albumin as a polymeric covering, with mass ratio 5-350 of $Fe_3O_4$ to 100 of albumin. The carrier provides rather fast release of a medical or biologically active material in an aqueous medium or blood, and if the microspheres are not attacked with proteolytic enzyme, the carrier conserves the integrity and activity for up to 48 hours.

The method has the disadvantage, as the used carrier has insufficient hydrolytic and enzymatic stability, and magnetizability.

The use of controlled methods of delivery of medical (therapeutic) agents by means of, for example, magnetic carriers is of high significance, as it allows delivery of a pharmaceutical to target organ under applied external magnetic field. The use of magnetic pharmaceuticals, generally, reduces toxicity of medical material, and also provides longer duration of action which allows to reduce doses of medical material. Furthermore, the present work has the theoretical importance, specifically it allows to propose, what pharmaceuticals (their structural analogues) may be used for administration of magnetoactive compounds.

Methods of administration of magnetoactive pharmaceuticals are known, based on encapsulation of an active material and magnetic component into a binding shell (Giano Guan, Lin Shi yin, Zhang Xizeng, Zhongguo uaxue zazhi, Chin Pharm. G.-1996.-31, V 1.-p. 27-29; T. M. Shvets, N. F. Kushchevskaja, E. V. Klochko, Vrach. Delo (Л ikap. Спрaвa), 1997. p. 37-78) and on sorption of pharmaceuticals on a surface of magnetic carrier particle (RU 2030618 and RU 2068703), and on administration of a magnetic component and formation on its surface of a polymeric covering into which a medical material is administered (RU 2065302; Formulation and characterization of magnetic poly(glutaraldehyde) nanoparticles as carriers for poly(1-lysinemethotrexate)/Hung C. T., Mcleod A. D., Gupta P. K.//Drug Dev. And Ind. Pharm.-1994.-16, 3. p. 509-521.; N. L. Lukjanchikova, L. I. Autenshljus, N. A. Brusentsov, Bull. Sib. Branch of AMS USSR, 1989.-1. p. 17-21). Highly effective pharmaceuticals are known, obtained by pelletizing of mixture of magnetic materials, antitumor pharmaceuticals (Fluorouracil, Bleomycin, Chromomycin) and adhesive water-soluble polymers (hydroxypropyl cellulose etc.) (Application 2-9813 Japan), and also drugs containing magnetic materials, along with their uses (Ito Ritsuko, Matida Isikharu, Yaminami Takanari.-6339599//J. of Chem. Abstr. 19. ChemistryVINITI-1991-60.-p. 76).

The method of delivery, for example, of Adriablastin with a magnetic carrier (RU 2018312, Aug. 30, 1994) is known. Technology is implemented by placing of Adriablastin on a ferromagnetic in aqueous solution with the use of freshly prepared magnetite or powder of reduced iron, as a ferromagnetic, which is preliminarily activated with 0.05 N solution of inorganic acid. Magnetite and aqueous solution of a therapeutic agent are prepared separately, and then deposition of the pharmaceutical on ferromagnetic powder is performed. This step is carried out as follows: a certain volume of aqueous suspension of synthetic magnetite or activated powder of iron, containing 1 g of dry ferromagnetic, is placed into reactor vessel supplied with a stirrer. Aqueous solution of Adriablastin with concentration $1-5 \times 10^{-4}$ M is added to the reaction mixture and stirred at 20° C. for 0.5-4 minutes. The resulted product separated from excess of aqueous medium by decantation.

Other method of delivery of pharmaceuticals with the use of magnetosensitive carrier is known. Magnetosensitive carrier consists of microcapsules prepared from high molecular weight organic compounds with magnetosensitive particles incorporated in them. A pharmaceutical is placed on the carrier and is used for treatment of tumor diseases with utilization of directed transport of an agent to a nidus by means of external source of magnetic field (K. Widder et al., J. of Pharm. Sci., 1976, v. 68, N 1, pp. 79-89).

However, the known magnetocontrolled microcapsules have not found any real life application in oncologic practice for some reasons:
  administration of magnetocontrolled microcapsules is associated with serious technological problems;
  the problem of standardization of the microcapsules, obtained by the known method, has not been solved;
  the problem of industrial manufacturing of microcapsules has not been solved.

Moreover, the method of administration of the known microcapsules assumes the use of aggressive media and/or high temperatures, which are incompatible with many pharmaceuticals. The essential component of the known microcapsules, high molecular weight organic compounds, represents a risk of development of allergic responses, population susceptibility to which increases during last years.

From RU 2143266, Dec. 27, 1999 the method of delivery (and treatments) of a pharmaceutical to a human organism is known with the use of magnetocontrolled carrier, comprising injection through a catheter connected to vessels, feeding a tumor tissue, pharmaceuticals, sorbed on ferrocarbon particles; localization of an agent in a nidus by means of a magnet placement on body surface projected on the tumor. The use of the magnet provides a gradient of magnetic density not less than $3$ T m$^{-1}$; and suspension of an antitumor agent administered with rate not higher than 1-2 ml min$^{-1}$ is used as a local chemotherapeutic and/or radiation antitumor agent. Localization of an agent in metastases takes place due to natural tropism of ferrocarbon particles to places of localization of tumor conglomerates, and after its magnetic localization in an area of tumor growth it is gradually biotransformed and the resulted complex compounds stimulate hemopoiesis and atrepsy.

However, the present method in a greater degree concerns delivery of a pharmaceutical at treatment of tumor diseases.

The method of delivery of pharmaceuticals controlled by magnetic field is known, in which stainless steel SUS 316L, covered with hydrogel of magnetic gelatin is used (Li-Ying Huang et al, Abstract PSTu-L-494 of ICM 2006, Kyoto, Japan, Aug. 20-25, 2006). Gelatin is intensively used in systems of delivery of pharmaceuticals due to its good swelling capacity and biocompatibility. Pore size of hydrogel may be controlled through a change of polymer composition, linkage conditions and concentration of magnetic precursor. Model pharmaceutical was introduced into gel film after application of magnetic field. Rate of release of the pharmaceutical noticeably decreased in comparison with the case of absence of the field. Apparently, it may be associated with denser configuration of hydrogel caused by aggregation of magnetic nanoparticles and decrease of gel pore size. The gel exhibited rather low cytotoxicity for L 929 cell line, which indicates its good biocompatibility. The used method shows good possibilities for biomedical devices as cardiovascular stent with delivery of pharmaceuticals, and also for tissue engineering.

Good example of application of heat-sensitive polymers for delivery of cells is the use of copolymer of N-iso-propyl acrylamide and acrylic acid for delivery of chondrocytes at maintenance of cartilage (J. Biomed. Mater. Res. A, 69, 2, 367-372, Au, etc). In such system temperature may change under applied magnetic field.

It is known, that heat-sensitive ferrofluids (type F 127), consisting, for example, from magnetic nanoparticles, covered with a shell from Pluronic F 127, may be used for desorption of pharmaceuticals controlled by a magnetic field (Ting-Yu Liu, et al, Abstract We A1-C2-3, ICM 2006, Aug. 20-25, 2006, Kyoto, Japan). It has been noted, that such F 127 ferrofluid forms gels at temperature above 23.8° C., which is noticeably below the one for pure Pluronic F 127 (40.5° C.). A pharmaceutical may be homogeneously distributed in F 127 ferrofluid below lower critical solution temperature and then at temperature above critical be encapsulated in the ferrogel. Heating of magnetic particles with alternating magnetic field may be used for formation of such gels (J. H. Park et al, J. Magn. Magn. Mater, 2005, v 293, p 328; D. H. Kim et al, J. Magn. Magn. Mater, 2005, v 293 p 320). Experiments have also shown that desorption of pharmaceuticals in similar gels may be also controlled by constant magnetic field. Release of vitamin $B_{12}$ was increased by 20% after application of magnetic field to the gel However, physical and chemical mechanisms leading to increase of desorption under applied constant magnetic field are unknown and, hence, cannot be controlled.

The method of utilization of alternating magnetic field, causing remagnetization of magnetic moments of particles and their subsequent heating is known and is used in hyperthermia.

Thus, there is a continuing necessity in providing novel compositions for controlled release rate drug delivery, for providing improved methods of delivery thereof to a human organism, and improved methods of manufacturing of drugs not only providing delivery of the active substance in a controlled way, but also the controlled release of the drug at a predetermined time and location in a patient's body.

BRIEF SUMMARY OF THE INVENTION

Thus, the object of the invention is to provide a method and pharmaceutical forms for controllable delivery of a pharmaceutical or a bioactive compound.

Still another object of the invention is to provide a magnetic carrier for pharmaceutical agents having enhanced effectiveness of delivery of a pharmaceutical to a designated place and enhanced effectiveness of localization in a designated place.

Still another object of the invention is to provide a magnetic carrier for chemical substances and medicinal agents, having improved retention/sorbtion capacity with respect to said chemical and pharmaceutical agents, and also improved controllability of subsequent release/desorption of one or several chemicals/pharmaceuticals in a designated place.

Still another object is widening the range of available magnetic carriers suitable for medical diagnostics, such as computer tomography.

One more object of the invention is providing magnetic carrier suitable for biological macromolecules (proteins and lipoproteins), cells, DNA, and similar biological objects.

Still another object of the invention is providing a carrier comprising magnetic nanoparticles encapsulated in polymers (poly(GMA)), which are capable of selectively bonding to other molecules under study.

The above and other technical objectives have been accomplished in the present invention by providing a carrier for active substances, suitable for use in pharmaceutical industry, as a carrier for bioactive materials, biological objects, for use in medicine in diagnostics and treatment, and for other uses.

According to the invention, the carrier for active substances comprises:
  at least one material A, which is magnetically or electrically sensitive, and
  at least one material B capable of controlling the retention/release rate of the said active substance from the said A carrier, the said retention/release rate being temperature dependent;
  wherein the at least one material B is in thermal contact with material A, and
  wherein the material A has magnetocaloric or electrocaloric effect sufficient to vary substantially the said retention/release rate of the active substance from the carrier.

Further, the invention relates to a magnetically responsive medical composition, comprising a therapeutic amount of active substance; and a carrier for active substances according to the invention. The medical composition can be prepared in the form adapted for injections, such as intravenous, intramuscular, trans-dermal, intra-bone injections, for topical application, such as patches, for oral administration, such as tablets, capsules, drage, e.g. formulated as a unit dosage form.

Especially preferable for a medical composition is the use of material A having the temperature of magnetic phase transfer within or around the interval comprising the temperature of an animal or human body.

The term "material A magnetically sensitive" means any material capable of spontaneous magnetic polarization in the absence of magnetic field in a certain temperature range, which is sensitive to external conditions.

The term "material A electrically sensitive" means any material capable of spontaneous electrical polarization in the absence of electric field in a certain temperature range, which is sensitive to external conditions.

The term "material B capable of controlling a retention/release rate" means that material B is selected from materials capable of influencing, in multiple ways, a retention/release rate of a substance from the carrier, whatever structure the carrier has and whatever type material B is. For example, an active substance can be adsorbed on material A, while material B can be a polymer encapsulating the material A, so that the release rate of the active substance from the carrier will be controlled by the penetration rate of the active substance through the polymer coating. Or, in case an active substance is dissolved in material B coated onto a material A, the release rate of the active substance from the carrier will depend on the solubility and diffusion rate of this substance in the polymer. Another case could be material B being a thermally sensible polymer exhibiting transition from insoluble to soluble form around LCST (low critical solution temperature), and the active substance being cells attached to the polymer surface above the LCST and "lift off" below LCST.

The term "temperature-dependent" means that the release rate varies with the increase/decrease of temperature significantly enough, by way of non-limiting example only, to be detected by sensors, or to change the speed of a chemical reaction, or to create a therapeutically efficient concentration in a patient organism, etc.

The term "in thermal contact" means that the two materials are in a contact providing a heat transfer from one material to the other, sufficient for material B to change its retention/release features when the temperature of material A changes.

The term "magnetocaloric or electrocaloric effect sufficient to vary substantially the said retention/release rate of the active substance from the carrier" means that the change of temperature by the material A shall be significant enough to cause the transition in material B to effect the release of active substance from the carrier.

According to the invention, material A is a magnetic, ferroelectric material or a combination thereof, for example material A can comprise two or more magnetic materials, or it can be a combination of magnetic and ferroelectric materials.

According to the invention, a magnetic material is selected from the group including but not limited to, rare earth metals, such as gadolinium, terbium, dysprosium, holmium, transient metals, such as iron, nickel, cobalt, magnesium, noble metals, such as rhodium, palladium; their oxides, compositions, combinations, solid dispersions, and alloys, such as $Gd_5Si_4$, $Gd_5Si_{2.06}Ge_{1.94}$, $Gd_7Pd_3$; $MnFeP_{0.35}As_{0.65}$ and MnAs. According to the invention, a ferroelectric material is selected form the group including compositions, complex oxides, alloys, solid dispersions and other combinations of elements of the IV group, including but not limited to lead, zirconium, titanium, tin, doped by small amounts of the elements of the III and V groups, such as scandium and niobium, including but not limited to the following materials: $PbZr_{0.95}Ti_{0.05}O_3$, $Pb_{0.99}Nb_{0.02}(Zr_{0.75}Sn_{0.20}Ti_{0.05})_{0.98}O_3$; $PbSc_{0.5}Ta_{0.5}O_3$ 0,9 $(PbMn_{1/3} Nb_{2/3}O_3)0,1(PbTiO_3)$, preferably in the form of a thin film.

According to one embodiment of the invention, material A consists of a magnetic or ferroelectric component, covered with a film of material B being a biocompatible heat-sensitive material (polymer).

According to another embodiment, material A is distributed in material B being a heat-sensitive medium, having properties changing at heating/cooling above/below the temperature of a human body.

According to still another embodiment, especially suitable for medical purposes, the magnetic or ferromagnetic component is made from a material with high magnetocaloric or electrocaloric effect and with phase transition temperature close to the temperature of a human body and selected from the group, which includes rare-earth, transition and precious metals, their alloys and intermetallic compounds.

In general, according to the invention, the magnetic or ferroelectric material can be employed in many other forms, both bulk and particulate.

The magnetic component or ferromagnetic material can be for example in the form having at least one dimension less than micrometer, preferably, from about micrometer to about nanometer, including nano-foil or nano-wire, for example, from gadolinium or $Fe_{0.49}Rh_{0.51}$ alloy.

The magnetic component or ferromagnetic material can be in the form of small size particles, down to nano-size, i.e. nanoparticles with sizes, for example, from several to 400 nm; preferably, from about 25 nm to about 400 nm, preferably, from 50 nm to 100 nm.

In another embodiment, the carrier may be in the form of carbon tubes filled with magnetic compound or ferromagnetic material.

The magnetic component or ferromagnetic material may be preliminarily placed on a substrate traditionally used in manufacturing, for example, inorganic substrates, preferably, from silicon dioxide or magnesium oxide; it may be also preliminarily covered with a protective layer, for example, of graphite or silicon dioxide, or glass, which prevents its possible further oxidation.

In still another embodiment, the material A and material B separately or together form a dispersion, such as suspension, aerosol, solution, colloidal solution, such as gel, including hydrogel.

Two or more magnetic or ferromagnetic materials with different values of magnetocaloric or electrocaloric effect may be used simultaneously. Moreover, two or more heat-sensitive polymers or mediums with different phase transition temperature may be used simultaneously.

According to the invention, the term "active substance" means a substance including but not limited to, a chemical agent, a pharmaceutical, a biologically active substance, biological object, a genetic construct.

In medicine, especially preferable active substances selected from the group including but not limited to anti-inflammatory agents, antibiotics, pain killers, anti-allergic, anti-histamine, anti-tumor, antivirus, anti-diabetic, anti-ulcer, anti-hyperlipidemic, anti-thrombosis agents, beta-blockers, vasodilators, bone resorbtion inhibitors and others.

The term "pharmaceutical" refers to a product, which includes all compounds, which cause a certain biological response. The term "pharmaceutical" refers to any drug administered to mammals, including, but not limited to, humans, domestic animals, wild animals and animals raised for the use of its meat, or other products such, as agricultural animals and cattle. The term "pharmaceutical" includes, but not limited to, the following classes of pharmaceuticals: therapeutic drugs, preventive drugs and diagnostic drugs. Examples of pharmaceuticals which may be implanted in a polymeric matrix, include but are not limited to: narcotic analgesic drugs; salts of gold; corticosteroids; hormones; antimalarial drugs; indole derivatives; pharmaceuticals for arthritis treatment; antibiotics, including Tetracyclines, Penicillin, Streptomycin and Aureomycin; antihelmintic and canine distemper drugs, applied to domestic animals and large cattle, such, as, for example, phenothiazine; drugs based on sulfur, such, as sulfioxazole; antitumor drugs; pharmaceuticals supervising addictions, such as agents controlling alcohol addiction and agents controlling tobacco addiction; antagonists of drug addiction, such, as methadone; weight-controlling drugs; thyroid gland controlling drugs; analgesics; drugs controlling fertilization or contraception hormones; amphetamines; antihypertensive drugs; antiinflammatories agents; antitussives; sedatives; neuromuscular relaxants; antiepileptic drugs; antidepressants; antidisrhythmic drugs; vasodilating drugs; antihypertensive diuretics; antidiabetic agents; anticoagulants; antituberculous agents; antipsyhotic agents; hormones and peptides. It is assumed, that above list is not full and simply represents the wide diversification of pharmaceuticals that may be incorporated in microparticles. Preferably, a pharmaceutical refers to a peptide.

The amount of drug distributed in a polymeric matrix depends on various factors including, for example, specific pharmaceutical; function which it should carry out; required period of time for release of a pharmaceutical; quantity of administered pharmaceutical and dimensions of an implant. Generally, dosage of a pharmaceutical, i.e. amount of pharmaceutical in microparticles, is selected from the range about from 0.5% (w/w) up to 95% (w/w), preferably, from about 5% (w/w) to about 75% (w/w), and, most preferably, from about 10% (w/w) to about 60% (w/w).

According to the invention, the active substance can be bonded either to material A and/or material B, or to both of material A and material B.

The term "bonded" herein includes but is not limited to adsorbed form, absorbed, solvated, dispersed, suspended, encapsulated form, linked by covalent bonds or Van-der-Vaals bonds, via linkers, peptide bonds, is enclosed within semi-permeable membrane, or bonded by mechanical bonds or physical bonds, such as by magnetic forces or electric forces, such as dipole-dipole bonds.

According to one embodiment of the invention, material B is a polymeric matrix which is a resolving (biodegradable) biocompatible heat-sensitive polymer.

In more general, material B is any temperature-sensitive (heat-sensitive) medium or a heat-sensitive compound, in particular, heat-sensitive polymeric films and heat-sensitive hydrogels. Polymers and copolymers with lower critical solution temperature may be used as heat-sensitive polymer. For example, the following chemicals may be used as heat-sensitive monomers: N-ethyl acrylamide, N-n-propyl acrylamide, N-n-propyl methacrylamide, N-isopropyl acrylamide, N-isopropyl methacrylamide, N-cyclopropyl acrylamide, N-cyclopropyl methacrylamide, N-ethoxyethyl acrylamide, N-ethoxyethyl methacrylamide, N,N-disubstituted (meth) acrylamide, such as N,N-dimethyl (meth)acrylamide and copolymers based on them.

N-substituted acrylamides and methacrylamides, O-substituted acrylamides and methacrylamides, and also other monomers, capable to copolymerize with monomers, which form heat-sensitive polymers, may be used as comonomers for heat-sensitive copolymers. Besides acrylamides and methacrylamides the following compounds with lower critical solution temperature may be used as heat-sensitive polymers: N-vinyl caprolactam and polyoxamers based on them, such as threeblock copolymers formed from polyoxyethylene and polyoxypropylene.

Besides the said polymers with lower critical solution temperature, biopolymers forming gel at increasing temperature, such as methyl cellulose, may be used. Heat-sensitive medium may be solutions and gels based on gelatin and collagen.

Heat-sensitive materials form solutions, gels, colloidal solutions, suspensions and dispersions with particles of magnetic or ferroelectric component, with the use of widely known in chemistry specific additives promoting their formation.

In particular, magnetic component may be a heat-sensitive ferrofluid, such as ferromagnetic fluid in the form of suspension of ferromagnetic particles in a bioactive fluid, for example, in extract of phytogenic bioactive compounds, in particular, in aloe extract; or in the form of ferrosilicon fluid.

Bioactive compounds in the embodiment of the invention are antigens, antibodies, nucleotides, gelling agents, enzymes, bacteria, yeast, fungi, viruses, polysaccharides, lipids, proteins, hormones, carbohydrates, cellular material. These are biosensing materials for development of biosensors prepared with the use of carrier, claimed as one of the embodiments of the invention.

Biosensors (biosensing elements, biochips), are designed for use in composition of, in particular, sensors for bioanalytical analysis in biotechnologies, in particular, in immunoassays, widely used in clinical diagnostics for detection of diseases or physiological conditions.

Biosensors traditionally include substrate, layer of sensing material evenly covering said substrate, the sensing material is specific to analyte species, and when biosensor contacts with medium containing the specified analyte, these species are bonded with the said sensing material.

According to the invention the substrate comprises a substrate from the list of materials, which includes plastics or glass, possibly, covered with metal, silicon wafers or foil, covered with the carrier, which is one of the embodiments of the invention.

The said sensing material is at least one of the following materials: antigens, antibodies, nucleotides, chelating agents, enzymes, bacteria, yeast, fungi, viruses, bacterial pili, components of bacterial flagella, nucleic acids, polysaccharides, lipids, proteins, carbohydrates, metals, hormones, aptamers, peptides and corresponding receptors to these materials.

Analyte species are, for example, at least, one of the following objects: bacterium; yeast; fungus; virus; rhematoid factor; antibodies IgG, IgM, IgA, IgD and IgE; carcinoembryonic antigen; group A *streptococcus* antigen; viral antigen; antigens, associated with the autoimmune disease; allergens; antitumor antigens; group B *streptococcus* antigens; HIV I or HIV II antigens; viral antibodies; antigens, specific to viral respiratory infections; antibody; antigen; enzyme; hormone; polysaccharide; protein; lipid; carbohydrate; pharmaceutical; nucleic acid; *Neisseria meningitides* groups A, B, C, Y and subgroups 135B; *Streptococcus pneumoniae; E. coli* K1; *Haemophilus influenza* type A/B; antigen, obtained from microorganisms; prostate-specific antigen and CRP antigen; hapten; a pharmaceutical supposing abuse; medical drug; environmental agents or hepatitis specific antigens.

The carrier of the invention obtained with the use of magnetic or ferromagnetic component with high magnetocaloric or electrocaloric effect in a combination with heat-sensitive material (a heat-sensitive biopolymer, heat-sensitive medium) may be also used for preparation of various implants, in particular, osteoblasts.

Human bone, treated by means of differentiated removing of the bone mineral for preparation of <<demineralized bones>> (DMB), is able to induce bone growth actively, when transplanted to a human (J. N. Kearney and R. Lomez, Advances in Tissue Banking, 1997, 1, 43-71). Such materials are widely used in odontology and maxillofacial surgery as the osteoinductive ability of such allogenic bones allows to carry out transplantation of primitive cells, precursors of mesenchyma to chondroblasts or osteoblasts (C. J. Yim, Advances in Tissue Banking, 1999, 3, 87-111). The method of the present invention allows to transform DMB into a compound with significantly enhanced osteoinductive activity, which accelerates formation and enriches quality of newly formed bone.

According to the invention the use of the carrier for preparation of implants, for example, osteoblasts, promotes stimulation of osteoblasts growth, speeds up delivery of these implants locally to a wound or a bone defect.

Such pharmaceutical implant is designed for controlled release of a pharmaceutical; after its administration in an organism with by means of applied magnetic or electrical field. It decomposes (first detached—desorbing from the substrate-carrier) to separate microparticles during certain necessary and defined period of time.

The invention, accordingly, also provides the implant designed for controlled release of a pharmaceutical into an organism of a patient. Pharmaceutical implant includes microparticles of one or several pharmaceuticals distributed in resolving (biodegraded) polymer (heat-sensitive medium), wherein the microparticles are sufficiently interrelated in order to maintain certain predefined form of the implant without complete adhesion of the polymer, and wherein the implant biodegrades into separate microparticles with time after administration, and wherein it covers a substrate-carrier, claimed in the invention.

The pharmaceutical content may be from about 0.5 to about 95% (w/w) of microparticles. Preferably, the pharmaceutical content is from about 5 to about 75% (w/w) of microparticles.

The said carrier, being one of the embodiments the invention may be used for administration of a substrate (covered with a heat-sensitive polymer) in cell technologies, and provides release of the cells cultivated on it (in vitro) [for their subsequent transplantation] without use of proteolytic enzymes and dissociating agents.

Copolymers of N-isopropyl acrylamide (NIPAAm) and N-tert-butyl acrylamide (tBuAM) are mainly used as heat-sensitive polymers.

The release of cells is provided by decreasing of ambient temperature below the critical point defined by the phase transition temperature in aqueous polymer solutions, using a magnetic or ferromagnetic material (component) with high magnetocaloric or electrocaloric effect, as a carrier of polymeric substrate.

The objective of the invention is also achieved by methods of controlled delivery of a pharmaceutical or therapeutic drug or bioactive compound to an organism, including the steps of:

administering into a human or animal body a medicinal composition comprising an active substance and magnetic or ferroelectric carrier, according to the invention;

localizing the said active substance in a predetermined place using magnetic, electric or other suitable properties of the carrier;

applying the external magnetic or electric field to effect cooling/heating of the magnetic or ferroelectric material to a temperature providing release of the active substance in a predetermined place and predetermined time.

A further objective of the invention is achieved by a method of treatment or prophylaxis of a disease or disorder in a patient in need of such treatment, by administering a medicinal composition according to the invention.

In one of a preferred embodiments, a method of treatment comprises the steps of:

administering a first active substance to a patient, wherein the first active substance is bonded to material A or material B and is capable of reacting with a second active substance;

wherein the first active substance is released at the predetermined time and/or pre-selected place when a second active substance is present in certain concentration in the organism or administered in certain concentration to the organism.

The medical composition according to the invention can be administered in courses.

In one more embodiment of the present invention, a method of administration of a pharmaceutical is provided, wherein the pharmaceutical consists of a medical drug or therapeutic drug, or a bioactive compound adsorbed on a magnetic material, or ferromagnetic material, covered with a film of heat-sensitive polymer, and/or distributed in other heat-sensitive medium, the method providing a controlled desorption of a pharmaceutical or therapeutic drug or bioactive compound due to phase transition from insoluble to soluble state at decreasing of medium temperature below critical point, as defined by the phase transition temperature of a polymer, and below the human body temperature.

Thus, according to the invention, a magnetic or ferromagnetic material is prepared from a material with high negative magnetocaloric or electrocaloric effect and its phase transition temperature is close to the human body temperature. A magnetic or ferromagnetic material is selected from the group, which includes rare-earth, transition and precious metals, their alloys and intermetallic compounds or oxides, for example, FeRh alloys. The objective is also achieved by localization of a medical or therapeutic drug or bioactive material in a target area. Decrease of temperature in a preset place, which causes desorption of a medical or therapeutic drug or bioactive material, is made by applied external magnetic or electric field and by cooling of magnetic or ferromagnetic material, which due to negative magnetocaloric and electrocaloric effect provides cooling of the heat-sensitive polymer or other heat-sensitive medium.

Magnetic or ferromagnetic material are particles of small size down to nanosize, furthermore, they may be prepared in the form of plates or foil, and, besides, magnetic or ferromagnetic material may be nanotubes filled with magnetic or ferroelectric material. The magnetic or ferroelectric material may consist from nanowires made of nickel or $Fe_{0.49}Rh_{0.51}$ alloy of 200 nm in diameter and 20 microns in length, they also may be prepared from magnetic nanoparticles, films or objects of other forms, other regulated or disordered bulk structure with large surface area and, hence, of high heat exchange, which prepared directly by application on a substrate. Magnetic or ferroelectric material may be preliminarily coated with a thin protective layer preventing its further oxidation. Correspondingly, the protective layer is prepared from graphite or silicon dioxide or glass.

The objective is also achieved by the methods of controlled delivery of a pharmaceutical or therapeutic drug or bioactive compound to an organism, including administration of pharmaceutical consisting of a medical drug or therapeutic drug, or a bioactive compound adsorbed on a magnetic material or ferromagnetic material, covered with a film of heat-sensitive polymer, and/or distributed in other heat-sensitive medium, which provides the controlled desorption of a pharmaceutical or therapeutic drug from a polymeric matrix due to phase transition from insoluble in a soluble state at increasing of medium temperature above critical point, defined by the phase transition temperature of a polymer, and above the human body temperature. Thus, a magnetic or ferromagnetic material is prepared from a material with high positive magnetocaloric or electrocaloric effect and its phase transition temperature is close to the human body temperature. A magnetic or ferromagnetic material is selected from the group, which includes rare-earth, transition and precious metals, their alloys and intermetallic compounds. The objective is also achieved by localization of a medical drug in a target area. Decrease of temperature of a media, for example, a polymer, which causes desorption of a medical or therapeutic drug or bioactive material, is made by initial heating of magnetic or ferromagnetic material by application of external magnetic or electric field to magnetic or ferroelectric material with high positive magnetocaloric or electrocaloric effect, which provides heating due to magnetocaloric or electrocaloric effect, with further natural cooling of magnetic or ferroelectric material down to temperature of adjacent tissues with final cooling of the magnetic material below the human body temperature, due to release of magnetic or electric field.

Magnetic material is gadolinium metal foil of 0.1 mm thickness. Ferroelectric with high electrocaloric effect (under applied external electrical field) may be prepared in the form of film based on $PbZr_{0.95}Ti_{0.05}O_3$ (Mischenko A. S., et. al, Science, 2006, v 311, p 1270-1271) or materials as $PbSc_{0.5}Ta_{0.5}O_3$ in a form of plates 20×10×0.5 mm (Y. V. Sinyavsky et. al., Ferroelectrics, 1989, v 90, pp. 213-217).

DETAILED DESCRIPTION OF THE INVENTION

Herein below particular embodiments of realization of the present invention will be described in details by wat of non-limiting examples relating to a carrier for pharmaceuticals, bioactive materials, bioobjects, methods of controlled delivery of pharmaceuticals comprising the carrier, and its use in methods of administration of pharmaceuticals. In the invention, an a carrier for active substances, such as medical (therapeutic) agents, comprising magnetic material in the form of magnetic or ferroelectric particles provides effective transportation (delivery), localization of a medical (therapeutic) agent and its controlled release into a target area under applied external magnetic or electric field, based on the, so-called, magnetocaloric or electrocaloric effect or due to heat released, for example, at demagnetization of magnetic particles by alternating magnetic field.

Magnetocaloric effect (MCE) or electrocaloric effect comprises heat liberation or heat absorption in magnetic or ferroelectric material under applied magnetic or electrical field. If these changes take place under adiabatic conditions they result in increasing or decreasing of sample temperature.

Magnetocaloric effect was discovered by Warburg in 1881. MCE is based on the ability of any magnetic material to change its temperature and entropy under applied constant magnetic field, as it takes place at gas or steam compression or expansion or, for example, in traditional refrigerators.

Change of magnetic material temperature takes place as a result of redistribution of internal energy of magnetic material between the system of magnetic moments of its atoms and crystal lattice.

Magnetocaloric or electrocaloric effect may be used, in particular, in technology of magnetic or electrical refrigeration, for example, in air conditioning of large space rooms, in food storage equipment, and, in particular, in manufacturing of refrigeration systems, both industrial, and household. Various magnetic materials are used as working bodies in magnetic refrigerators functioning on the principle of magnetocaloric cooling.

Magnetocaloric effect, in particular, determines magnetocaloric properties of magnetic materials, and the higher the effect is, the more effective is liberation or absorption of heat in magnetic materials under magnetic field. This leads to extension of functionality of magnetic materials and increase of efficiency of medical preparations delivery to a target place and, in particular, efficiency of magnetotherapy of various diseases, for example, magnetotherapy of malignant neoplasms.

Examples of the materials used in the claimed method, with high magnetocaloric effect and with phase transition temperature close to the human body temperature (from 36° C. up to about 37° C.) are reported in details (A. M. Tishin, Y. I. Spichkin Magnetocaloric effect and its application, Institute of Physics Publishing, Bristol and Philadelphia, 2003, pp. 410-411). In particular, there are alloys based on precious metals (rhodium, palladium, platinum), rare-earth elements (metals), as, for example, gadolinium Gd (Curie temperature about 295 K and MCE value $\Delta T=5.8$ K at $H=2$ T), alloys or their intermetallic compounds, as, for example, iron-rhodium alloy $Fe_{0.49}Rh_{0.51}$ (magnetic phase transition temperature of antiferromagnetism-ferromagnetism is about 310-316 K and MCE value reaches minus 13 K in the field of 2 T); gadolinium-silicon alloy $Gd_5Si_4$ (with temperature of maximum MCE value $\Delta T=8.8$ K at $T=336$ K and $H=5$ T); gadolinium-silicon-germanium alloy $Gd_5Si_{2.06}Ge_{1.94}$ ($\Delta T=8$ K in the field of 5 T and at $T=306$ K); gadolinium-palladium alloy $Gd_7Pd_3$ ($\Delta T=8.5$ K at $T=323$ K and $H=5$ T); manganese-iron-phosphorus-arsenic alloy $MnFeP_{0.35}As_{0.65}$ (maximum of MCE $T=332$ K); manganese-arsenic alloy MnAs ($\Delta T=13$ K at $T=318$ K and $H=5$ T) and others.

Ferromagnetic material may be films based on material of the type $PbZr_{0.95}Ti_{0.05}O_3$ or $Pb_{0.99}Nb_{0.02}(Zr_{0.75}Sn_{0.20}Ti_{0.05})_{0.98}O_3$ (Mischenko A. S., et. al., Science, 2006, v 311, pp. 1270-1271) or materials of the type of $PbSc_{0.5}Ta_{0.5}O_3$ (Y. V. Sinyavsky et. al., Ferroelectrics, 1989, v 90, pp. 213-217).

Both materials are used with chemical additives allowing shifting the temperature range, where high electrocaloric effect is observed, to the range of the human body temperature. The electric field up to 25 V is applied during desorption process. The temperature of a ferroelectric may vary up to 10-12° C. (i.e. 0.48 kV-1) A. S. Mischenko, et al., Science, 2006, v 311, pp. 1270-1271.

Other example of ferromagnetic material may be 0.9 $(PbMn_{1/3}Nb_{2/3}O_3)0.1(PbTiO_3)$. Under applied electrical voltage of $V=25$ V the effect comprised 5 K at 60° C. (A. S. Mischenko et al, arXive:cond-mat/0604268. v1, 11 Apr. 2006). In materials of the type of $PbZr_{0.95}Ti_{0.05}O_3$ the electrocaloric effect reaches value $\Delta T=1.4$-$1.8$ K at $E=15$-$25$ kV $sm^{-1}$ and slightly decreases with increase of temperature (Y. V. Sinyavsky et. al., Ferroelectrics, 1989, v 90, pp. 213-217).

Such magnetic materials or ferroelectric are used in the form of plates, foil or in the form of particles with sizes, for example, from 100 nm to 400 nm. From magnetic measurements it is known, that temperatures of magnetic phase transitions strongly depend on concentration of alloyed metals and elements in alloys and compounds of rare-earth metals (REM). It is possible to achieve the required magnetocaloric effect and to provide required temperature, for example, of magnetic phase transition, close to the human body temperature, by variation of the content of a certain element in the alloy. Generally, for example, magnetic phase transition takes place in a wide range of magnetic fields with magnetic strength from several kE up to 60 kE (kiloerstad) and more.

Particles of a magnetic or ferroelectric material are prepared using various known technologies, for example, by the plasma method in inert medium (for example, under argon) from particles of one or another metal (element) with initial size, for example, 50-100 microns, or, for example, similar to the method disclosed in SU 1746162, Jul. 7, 1992, or by deposition of nanoparticle layer on a substrate.

In the embodiment of the invention particles of carbon (graphite) may be deposited on ferroelectric or magnetic particles, mentioned above, by known methods (for example, from SU 1722256, 1991). They may be used in the form of carbon nanotubes, filled or covered with ferroelectric or magnetic particles of materials with high magnetocaloric or electrocaloric effect. Then a heat-sensitive polymer is placed on their surface. Particle size is varied within the range from ultradispersible to nanosize.

Furthermore, heat-sensitive polymer is applied, for example, on the magnetic carrier, and medical therapeutic drugs are being adsorbed on the former. Drugs are, for example, in the form of suspension and are delivered to the defined place by applying of external magnetic field with the use of magnetic particles with high magnetocaloric effect (MCE). The used magnetic particles should have high powder dispersity, which provides free moving of the carrier with a pharmaceutical in vessels when administrated in vitro; possess saturation of magnetization, sufficient for control of moving of the carrier with a pharmaceutical with a source of an external magnetic field of rather low intensity; provide controlled delivery of a drug to a target (preset) place. All this is provided by the use of magnetic particles with high negative or positive magnetocaloric effect.

The pharmaceuticals delivered to an organism of a human by the method of the invention are various medical products, drugs, enzymes, for example, such as Adriablastin, Adriamycin, riboflavin (vitamin $B_2$), novocain, Chinosolum, such antitumoral drugs as Fluorouracil, Bleomycin, Chromomycin and other medical and therapeutic drugs. Concentration of the resulting pharmaceutical may be also different depending on its type and action, as the pharmaceutical is used either in the form of aqueous solutions, or in the form of solutions, suspensions in physiologically adequate carrier.

In particular, the heat-sensitive polymer (as follows from above) in this case is a polymer, which desorption properties are increased at heating due to the phase transition from insoluble state to soluble state. Thus, medical (or therapeutic) product may consist of two active pharmaceuticals, capable, if necessary and under certain conditions (for example, in contact and influence of an external magnetic or electrical field), to interact with each other, enhancing in such a way their medical action; and only one (first) reacting pharmaceutical is adsorbed on the carrier (described above) and its desorption is carried out, if necessary, at a moment of time and/or in a defined place, when the second reacting pharmaceutical (or bioactive material) is administered into an organism (or already is present in an organism).

In the method of the invention the heat-sensitive polymer, which provides controlled desorption of a medical or therapeutic drug or bioactive material in a preset place (its localization), is, for example, poly-N-isopropyl acrylamide (co) polymers, other (co)polymers of (meth)acrylamide, for example, propyl methacrylamide, polymers containing ethylene oxide groups, cellulose derivatives, for example, ethyl hydroxyethyl cellulose, cellulose acetate and others.

Formation of films of the heat-sensitive polymer on a magnetic or ferroelectric material (substrate, carrier) is made, for example, from alcohol solutions of polymers. The heat-sensitive substrate is obtained on which surface the medical or therapeutic drug or bioactive material is then sorbed.

Eliminating (desorption) of a pharmaceutical is performed at decrease of temperature of a medium below the critical value defined by transition temperature of polymer in aqueous solution. Heat-sensitive polymers undergo phase transition from water insoluble (solid substrate) to soluble state at the temperature called the lower critical solution temperature (LCST).

The thickness of the heat sensitive polymer film is from about 10-20 nm to 100 micron depending on the thickness and physical form of the magnetic material. In general, the thickness of the polymer film is 10-20% of the diameter of a magnetic particle to enable fast and effective desorption/release of a pharmaceutical from the polymer film. In case a magnetic material is a metal foil, the thickness of the polymer film can be from about 100 nm to 100 micron.

The content of magnetic or ferroelectric particles in the carrier can vary from 1 up to 99 wt % to provide the sorption capacity from 3.0 up to 96%, correspondingly. The sorption capacity is estimated by mass of sorbed dye, methylene blue. Magnetic or electrical sensitivity of magnetic or ferroelectric particles depends on chemical composition of magnetic or ferroelectric particles.

The resolving (biodegradable) polymer may represent a polymer of lactic acid, glycolic acid, polyethylene glycol, poly-(ortho-ester), polycaprolactones or their copolymers.

Pharmaceutical implant may additionally include one or more additives. Additives may be resolving (biodegradable) polymers, mannitol, starch sugar, inosite, sorbitol, glucose, lactose, saccharose, sodium chloride, calcium chloride, amino acids, magnesium chloride, citric acid, acetic acid, hydroxyl-butanedioic acid, phosphoric acid, glucuronic acid, gluconic acid, poly-sorbitol, sodium acetate, sodium citrate, sodium phosphate, zinc stearate, aluminium stearate, magnesium stearate, sodium carbonate, sodium bicarbonate, sodium hydroxide, polyvinylpyrolidones, polyethylene glycols, carboxymethyl celluloses, methyl celluloses, starch or their mixtures.

Pharmaceutical implant may be of cylindrical form from about 0.5 to about 5 mm in diameter and from about 0.5 to about 10 cm in length. Preferably, its diameter is from about 1 to about 3 mm and length from about 1 to about 5 cm.

The cultivated cells are used, for example, fibroplasts of line NCTC clone L 929. Cells cultivated in medium "Needle", Dulbecco modification, containing 10% of embryonal veal serum (EVS), 50 μg ml$^{31\ 1}$ of Penicillin, 50 μg ml$^{-1}$ of Streptomycin and 1% L-glutamine at 37° C. in the wet atmosphere containing 95% of air and 5% of $CO_2$.

Below are the examples illustrating, but not limiting, the embodiment of the invention.

EXAMPLE 1

For example, the polymer poly-N-isopropyl acrylamide is in a solid (insoluble) state at T=37° C., which allows to use it as solid substrate on which a pharmaceutical, for example, immunoglobulin may be sorbed. Decrease of temperature below LCST, for example, down to temperature about 32.5° C. for the above-stated polymer, causes hydration of the polymer and release of the pharmaceutical, immunoglobulin, from the surface of substrate. Heat-sensitive polymers have LCST in the physiological range. Depending on the nature of polymer, a comonomer ratio in a copolymer, it is possible to vary LCST value. For example, LCST for polymer N-isopropyl acrylamide is 32.9° C., for its copolymers with N-tert-butyl acrylamide (tBuAM) LCST varies from 25.2° C. (15% tBuAM) to 9.6° C. (50% tBuAM). Desorption is stopped with removing of external magnetic field and is proceeded at repeated application of it, and so up to the full desorption of a pharmaceutical.

The carrier claimed in the invention is prepared from quickly quenched alloy $Fe_{0.51}Rh_{0.49}$ with high negative magnetocaloric effect. The value of magnetocaloric effect in the alloy at temperature 310 K is about 4.9 K/T. Particles of the alloy of 90-120 nm were covered with a film of biocompatible heat-sensitive polymer—poly-N-iso-propyl acrylamide, on which surface the pharmaceutical (immunoglobulin) was sorbed.

The method of delivery of this medical anesthetizing agent according to the invention is carried out as follows. Magnetocontrolled pharmaceutical is administered and magnetic field of 1 T is applied.

At the first step the adsorption of photoinitiator on the surface of particles of magnetic material was performed. For this purpose, first, aqueous solution of photoinitiator $0.5 \times 10^{-4}$ M was prepared. Then adsorption of Riboflavin on the surface of particles was achieved by their shaking with aqueous solution of Riboflavin. The quantity of the adsorbed Riboflavin was determined by the analysis of contacting solution by UV-vis spectroscopy, after preliminarily plotted graph of optical density at 440 nm as a function of the solution concentration. According to the analysis results, the content of photoinitiator on the particles surface corresponds to 1.5-2.0 monomolecular layers. Then particles of the magnetic material were introduced into a quartz reactor supplied with a stirrer, which was preliminarily loaded with 2% solution of acrylamide in glycerin with addition of crosslinking agent—N,N-methylene-bis-acrylamide and Novocain. Synthesis was carried out at continuous stirring and irradiation of the reaction mixture with a powerful source of visible light during 2-3 hours at temperature 25° C. The quantity of novocaine imbedded in the net of crosslinked polyacrylamide, obtained on the surface of magnetic particles, was determined by UV-spectroscopy on absorption bands at 220 and 290 nm from analysis of the contacting solution after synthesis. The Novocain content in the resulted synthetic product is 2.50 wt % of polyacrylamide coating of magnetic material. The thickness of polyacrylamide film embedded with Novocain was from about 200 to about 500 nm.

Study of anesthetic activity of the drug was performed on 5 rabbits of 2.0-2.5 kg weight under conditions of acute experiment. (V. A. Trotsevich). Clinico-pharmacological study of the anesthetic effect of pharmaceuticals and their combinations, was performed on the CHN analyzer from PerkinElmer (USA). The content of novocaine imbedded in the net of crosslinked polyacrylamide, obtained on the surface of magnetic particles was determined on the basis of analysis of contacting and wash liquids by UV-spectroscopy (absorption band of novocaine at 290 nm). Anesthetic activity tests of the drug <<Ferrocaine>> were performed on 5 not purebred rabbits by measurement of the evoked potential according to the above described procedure.

For preparation of the anesthetizing agent with prolonged action, with increased duration of anesthetizing action the following materials were used:

Novocain of technical specifications (TU) 64-3-167-84

Acrylamide (pure), $CH_2=CHCONH_2$, Interstate technical specifications (MRTU) 6-09-356-63

N,N-methylene-bis-acrylamide (pure) $CH_2(NHOCCH=CH_2)_2$ technical specifications (TU) 6-09-195-70

Glycerin, $HOCH_2CHOHCH_2OH$, (analytical reagent) GOST 6259-52

Ethanol, $CH_2CH_3OH$, technical specifications (TU) IREA 20-66

Water distilled Interstate technical specifications (MRTU) 6-09-688-63

Riboflavin, vitamin $B_2$, product of <<Sigma Chemical Company>>, USA.

Particles of magnetic material with high magnetocaloric effect—iron-rhodium alloy $Fe_{0.49}Rh_{0.51}$ (maximum MCE reaches minus 13 K in the field of 2 T) are obtained, for example, using one of the known procedures by means of mechanochemistry.

Dextran is introduced before administration of a drug for intensifying its anesthetizing action in an organism.

EXAMPLE 2

Duration of anesthetizing action of an anesthetizing agent may be increased by using the carrier of the invention, one of the medical materials, when, for example, novocaine is absorbed on the carrier and then the material is released by the method of the invention through desorption at necessary time and in a necessary place at administration of the second medical material, for example, dextran.

It is known, that Novocain does not exhibit anesthetizing action during sufficiently long period of time.

It was found that products of interaction of novocain and dextran possess properties providing their use in therapeutic practice as anesthetizing pharmaceuticals for local long-term action. The Novocain content in a final product is 0.1-95.0 wt %, mainly 1-30 wt %. Syntheses of novocaine and dextran were carried out by activation of hydroxyl groups of dextran by cyanogen bromide, forming cyclic iminocarbonates, which form homopolar bonds with para-amino group of novocaine.

In this example the carrier is prepared from the following material: heat-sensitive ferrofluid based on alloy $Fe_{0.51}Rh_{0.49}$, heat-sensitive medium—polyacrylamide. Particles of the magnetic material are covered with polyacrylamide shell (cross-linked). The thickness of polyacrylamide film embedded with Novocain was from about 500 to about 750 nm.

Accordingly, the enhancement of medical effect may be achieved by delivery of various pharmaceuticals to an organism with the claimed method.

For example, one of the pharmaceuticals adsorbed on the carrier (as active material), for example, as liposomes, in the form of pharmaceutical drug, and, in particular, anti-inflammatory, antiseptic or wound-healing and antibiotics are the second medical material administered into an organism. Enhancement of the medical effect takes place due to possible interactions between them, during release (desorption) of one of them (first) and administration (at necessary time and place) of another.

It is also possible to administer (for example, in gastrointestinal tract), as an active compound, microbial mass of viable bifidobacteria, adsorbed on the carrier claimed in the invention, with subsequent desorption of them by the claimed method of delivery. At administration of the second medical material, for example, bioactive ingredients of immunomodulating, regenerating and protective actions. The drug may contain lysozymes, interferons, immunoglobulins, hyaluronic acid, bioactive peptides, bifidobacteria growth factors and also antimicrobial, anti-virus or antimycotic agents.

It is necessary to note, that bifidobacteria, as a part of compositions or independently, are applied for establishment and maintenance of the normal intestinal flora, for regulation of an intestinal microflora, treatment of an intestine dysbacteriosis, dysentery, infantile colic, reactive postinfectious arthritis, atopic dermatitis, for administration of immunomodulating factor, for decrease of urea concentration in an organism, for regulation of cholesterol level in blood plasma, for biological deodorization etc. (DE 2755037 AL, EP 0482530 A3, SU 1286212 AI, SU 1258414 AI, DE 3716938, SU 1553132 AI, SU 1816215 A3, RU 2023445, DE 3406772 AI, EP 0181170 BI, EP 0208818 BI, EP 0228861BI).

Application of binary drugs, with both sorbed by the method stated above, is also possible. The release of both, pharmaceutical or chemical, compounds takes place in a target place simultaneously. Then their interaction and subsequent influence on an organism or an organ result in the expected therapeutic effect at necessary moment. Each of these agents or materials separately is bioinert and does not impact solely on a human organism.

Use of the binary approach is also possible for the following purposes. On the first substrate a pharmaceutical is absorbed, which either enhances the effect of an agent or agents placed on another substrate, or mitigates its action consequences, or has, for example, another time of action, compared with the first agent.

In case of administration of superpotent drugs in capsules it is also possible to use the first component for destruction of a material of a capsule with the release of the second component (pharmaceutical) simultaneously or shifted in time.

Application of heat-sensitive polymers with different temperatures of phase transitions for each component is also possible. It may result, for example, in that the first component will be released under applied field of 1 T and the second at 2 T.

EXAMPLE OF SPECIFIC REALIZATION 4

The method may be realized, for example, as follows: quenched magnetic material $Fe_{0.49}Rh_{0.51}$ covered with a heat-sensitive polymer together with a pharmaceutical (for example, anti-inflammatory) in the form of particles in of about 150-200 nm is administered inside of an organism through a catheter and delivery of the aforementioned particles is performed to a target organ or a tissue. Magnetic field of 2 T is applied on the area, where the particles are concentrated. The magnetic material is cooled by 13° C., which results in refrigerating of a heat-sensitive polymer, for example (co)polymer N-iso-propyl acrylamide, down to temperature below LCST, in this case down to 24° C., and desorption of the pharmaceutical from the surface of heat-sensitive polymer takes place.

EXAMPLE OF SPECIFIC REALIZATION 5

The method may be implemented, for example, as follows: particles of magnetic material $Gd_5Si_{2.06}Ge_{1.94}$ having diameter about 250-300 nm and the phase transition temperature about 306 K (Gschneidner K. A., Jr. and Pecharsky V. K., 2002, in Intermetallic Compounds—Principles and Practic ed J. H. Westbrook and R. L. Fleischer, New York, Wiley, v.3), are covered with a heat-sensitive polymer film to the thickness of about 25-50 nm (not more than 10-20% of the particle diameter) comprising a pharmaceutical (antitumor) composition embedded in the film. The particulate magnetic material prepared as described above is administered to an organism through a catheter, in particular, by applying magnetic field having the intensity of 3 T. The magnetic material is magnetized adiabatically (by means of fast switch of constant magnetic field), which causes increase of temperature at value of magnetocaloric effect ($\Delta T=4.5$ K at T=310 K), i.e. heating takes place; further, the magnetic material cools down due to heat exchange with blood and tissues; then, magnetic field is removed and adiabatic demagnitizaion takes place, refrigerating the heat-sensitive polymer, for example, (co) polymer N-iso-propyl acrylamide, down to temperature below LCST, in this case down to 32.6° C. and eliminating the pharmaceutical (its release, desorption) from the surface of heat-sensitive polymer film.

At realization of the claimed methods the following materials are used: magnetic field formed by a system of permanent magnets (magnetic field), working magnetic material in the form of particles and also auxiliaries, which provide, if necessary, administration of a magnetic material into a tumor, its transportation and concentration in a defined place.

The magnetic field may be also formed, for example, by superconducting solenoid. Concentration of particles in a certain place of tumor raises in advance due to applied magnetic field.

EXAMPLE OF SPECIFIC REALIZATION 6

Particles of a magnetic material, concentrated in a tumor, are evenly warmed up under applied magnetic field. When they warm up surrounding tissues, due to MCE heat production or due to remagnetizing of alternating magnetic fields, up to 40-42° C. (313-315 K), cancer cells perish. Then particles cool down to initial temperature close to the human body temperature due to heat exchange with surrounding tissues; further particles of material demagnetize due to removal of permanent field (cool) and refrigerate the heat-sensitive polymer. After temperature decrease there is desorption of pharmaceutical from the surface of polymer; and after the recurrent magnetization is possible. Accordingly, they are again heated up under applied magnetic field to the necessary temperature and consequently warm up the injured tissues, i.e. the method is based on the certain thermodynamic cycle.

Simultaneously with delivery of a pharmaceutical to tumors the sessions of magnetotherapy (hyperthermia) are performed by the methods of the invention, which help (together with pharmaceuticals) to kill cancer cells, keeping healthy cells safe.

EXAMPLE 7

A procedure analogous to that described in Example 4, but administration of a pharmaceutical Adriablastin in an organism is made, when the magnetic carrier represents alloy of iron-rhodium $Fe_{0.49}Rh_{0.51}$, which surface is covered with copolymer NIPAAm with 35 mol % of tBuAM film, with alloy surface preliminary covered with a thin protective graphite layer (preventing oxidation); the magnetic material is prepared in the form of plates.

After delivery of a pharmaceutical to an organism and its localizations according to the claimed method its desorption is performed by refrigerating of a substrate with the film made of thermoplastic polymer down to temperature below LCST—in this case to temperature 15.9° C. Time of desorption is 30±5 minutes.

EXAMPLE 8

A procedure analogous to that described in Example 4, but carbon nanotubes (20-30 nm and up to 1 mm in length), covered with magnetic iron-rhodium $Fe_{0.49}Rh_{0.51}$ particles of about 100 nm, are used as particles of the magnetic carrier.

EXAMPLE 9

A procedure analogous to that described in Example 7, but gadolinium nanowires of 20 microns in length and 200 nm in diameter are used as magnetic material. The thickness of polymer film was from about 10 to 30 nm.

EXAMPLE 10

A procedure analogous to that described in Example 7, but two different (or same, but modified) heat-sensitive polymers with different temperatures of phase transition differing in 5° C. are simultaneously used. Release of a pharmaceutical from the first polymer with higher point of phase transition takes place under applied field of 1 T ($\Delta T=-5-6$ K), and desorption of the second under applied field of 2 T ($\Delta T=-13$ K).

EXAMPLE 11

A procedure analogous to that described in Example 7, but alloys $Fe_{0.49}Rh_{0.51}$ and $Fe_{0.47}Rh_{0.53}$ are used simultaneously as magnetic carriers. Different formulation constituents are sorbed on these alloys. As value of MCE in these alloys differs in approximately 3 K under applied field of 1 T, refrigeration of the $Fe_{0.47}Rh_{0.53}$ alloy by 3.5 K will take place without phase transition in heat-sensitive polymer and desorption of the first drug. In exactly same polymer covering $Fe_{0.49}Rh_{0.51}$ alloy, phase transition will take place further under field of 1 T, as this alloy will cool down by 6.5 K and, hence, there will be desorption of one of components of a pharmaceutical or chemical. Under 2 T $Fe_{0.47}Rh_{0.53}$ alloy will cool by 7 K, which result in desorption of the second component.

EXAMPLE 12

A procedure analogous to that described in Example 5, but instead of magnetic material a ferromagnetic material, a thin film based on modified material of the type of $PbSc_{0.5}Ta_{0.5}O_3$ is used. Modification allowed shifting the range of temperatures, where high values of electrocaloric effect are observed, to the temperature range of human body. Electric fields applied in the desorption process are up to 25 V. Temperature of the ferroelectric changes by 5-5.3 K and the film thickness is about 2 microns.

EXAMPLE 13

Use of the Carrier as a Biosensor According to One of the Embodiment of the Invention The biosensor includes the substrate-carrier, claimed as one of the embodiments of the invention, to which bioactive materials, for example, *H. Pylori* antibodies or antigen-binding fragments are attached, which together with biomolecules of a heat-sensitive medium (with repelling biomolecules) form a layer of a sensing material, specific to an analyte object, such as bacteria, yeast, viruses, antibodies IgG, IgM, IgA, IgD and IgE, carcinoembryonic antigen, group A *streptococcus* antigens, viral antigens, antigens, associated with the autoimmune disease, allergens, antitumor antigens, group B *streptococcus* antigens, HIV I or HIV II antigens, viral antibodies, antigens, specific to viral respiratory infections, antibody, antigen, enzyme, hormone, polysaccharide, protein, lipid, carbohydrate, pharmaceutical, nucleic acid, *Neisseria meningitides* groups A, B, C, Y and W subgroup 135, *Streptococcus pneumoniae, E. coli* K1, *Haemophilus influenza* type A/B, antigen, obtained from microorganisms, prostate-specific antigen and CRP antigen, hapten, pharmaceutical supposing abuse, pharmaceutical, environmental agents or hepatitis specific antigens.

Further an interaction of biological sample obtained from a patient, suffering from an infection, with a biosensor takes place under applied external magnetic or electric field. The signal appearing at formation of an antibody-antigen complex is detected.

It is then shown, that preparation of the biosensor for chemicals detection in fluids under analysis is based on cultures of stem cells of rat's gustatory receptors.

The initial cell culture, enriched by olfactory receptors, is isolated preparatively from rat's tongue. The lines of stem cells are isolated from initial cell culture. The stem cells differentiated into cells of gustatory receptor, are morphologically detected by means of optical and electron microscopies (see, for example, Mandairon N, Jourdan F, Didier A. Deprivation of sensory inputs to the olfactory bulb up-regulates cell death and proliferation in the subventricular zone of adult mice. Neuroscience. 2003; 119 (2):507-16). The prepared sensory cells are placed into containers with a nutrient medium, as a part, for example, of the magnetic carrier of the invention, connected to an external device. Intrinsic electric activity of the sensory cells is registered. Calibration of the biosensor is slightly complex, as the used sensory cells contain complex assemblies of receptor molecules, each of them is responsible for reception of special group of chemicals. The descendants of various stem cells may possess various sensitivity patterns. Therefore, it is necessary to not allow uncontrollable mixture of sensory cells—descendants of various stem cells in structure of a biosensor. Calibration is carried out by method of addition of pure compounds or mixtures of chemicals, responsible for "bitter", "acidic", "salty", etc. sensation spectra or materials with strong or irritating smell, to a fluid medium, where the biosensor is deposited. Application of the prepared cells on the carrier and calibration of the biosensor are performed using a wide range of chemicals, which may be added either to a fluid medium, covering sensory cells of the biosensor with a thin layer, or to a closed, whenever possible minimal, volume of gaseous medium, where sensitive cells of the biosensor are placed. In the latter case it is necessary to increase exposure time of analytes in order to allow their diffusion through a thin layer of fluid medium, covering the sensory cells.

Building of new generation of the sensor devices based on use of the carriers under the invention and biological receptors and/or their parts for detection of incoming signals, is a relevant problem of biotechnology. Such sensors could combine compactness, high sensitivity and environmental safety with functioning in standard temperature range and relative inexpensiveness. Biosensors could be used for scientific, household purposes and also for detection of various types of electromagnetic radiation and presence of various chemicals in media under analysis. Development of nanotechnologies allows creation of carriers effectively receiving, amplifying, transducing and transferring signals from isolated receptor cells. Being organized in an ordered structure, such containers-carriers would be sensor device with sensitivity defined by the choice of used cells-receptors. At the same time, the approaches existing in the field are limited by use of receptors taken directly from an organism-donor, without a possibility of artificial generation of cells-receptors from replicated cellular cultures.

Magnetic or electrical field is used as an external device.

INDUSTRIAL APPLICABILITY

The present invention allows to increase efficiency of delivery of a pharmaceutical to a human organism, to increase degree of its localization in a preset place and then to perform controlled desorption of a pharmaceutical during a short period of time due to utilization of a magnetic or ferroelectric material with high positive or negative magnetocaloric or electrocaloric effect, providing refrigerating of a heat-sensitive polymer below the LCST and desorption of a pharmaceutical or bioactive material.

We claim:

1. A magnetically responsive medical composition, comprising:
   therapeutically effective amount of a pharmaceutical active substance; and
   a carrier for controllable delivery of a pharmaceutical active substance to a designated place within a patient's body, comprising:
      at least one material A having a positive or negative magnetocaloric or electrocaloric effect in the range of 1 to 13 K, which comprises
         a magnetic material selected from $Fe_{0.49}Rh_{0.51}$, $Gd_5Si_4$, $Gd_5Si_{2.06}Ge_{1.94}$, $Gd_7Pd_3$, $MnFeP_{0.35}As_{0.65}$, MnAs, and/or any combination thereof; and/or
         a ferroelectric material selected from $PbZr_{0.95}Ti_{0.05}O_3$, $Pb_{0.99}Nb_{0.02}(Zr_{0.75}Sn_{0.20}Ti_{0.05})_{0.98}O_3$, $PbSc_{0.5}Ta_{0.5}O_3$, $0,9(PbMn_{1/3}Nb_{2/3}O_3)0,1(PbTiO_3)$ and/or any combination thereof; and
      at least one material B, which is a heat-sensitive medium or compound selected from the group comprising polymers, copolymers, polymeric films, biopolymers and hydrogels, said material B controlling the retention/release rate of the said active substance from the said carrier, the said retention/release rate being temperature dependent;
      wherein said at least one material B is in thermal contact with material A, so that when subjected to magnetic or electric field the material A due to said magnetocaloric or electrocaloric effect causes a phase transition of material B providing the release of said pharmaceutical active substance from the carrier.

2. A carriar of claim 1, wherein material A is in the form of nanoparticles having dimensions from about 25 nm to about 400 nm.

3. A carrier of claim 1, wherein material A is in the form of a foil or thin plates.

4. A carrier of claim 1, wherein the material A has a temperature of magnetic or ferroelectric phase transfer in the range of 33 to 37° C.

5. A carrier of claim 1, wherein the material A comprises two or more magnetic or ferroelectric materials, which differ in value or polarity of magnetocaloric or electrocaloric effects.

6. A carrier of claim 1, wherein the material A is covered by graphite, silicon dioxide, and/or glass.

7. A carrier of claim 1, wherein the polymer is biocompatible and/or biodegradable polymer.

8. A carrier of claim 1, wherein the material B is a thermally sensitive polymer having a transition from insoluble into soluble state upon heating above the critical solution point or transition temperature, while material A has a positive value of magnetocaloric or electrocaloric effect, sufficient to achieve the transition temperature or critical solution point of the material B.

9. A carrier of claim 1, wherein the material B is a thermally sensitive polymer having a transition from insoluble into soluble state upon cooling below the critical solution point or transition temperature, while material A has a negative value of magnetocaloric or electrocaloric effect, sufficient to achieve the transition temperature or critical solution point of the material B.

* * * * *